United States Patent [19]
Johlin, Jr. et al.

[11] Patent Number: 5,241,970
[45] Date of Patent: Sep. 7, 1993

[54] PAPILLOTOME/SPHINCTEROTOME PROCEDURES AND A WIRE GUIDE SPECIALLY SUITED THEREFOR

[75] Inventors: Frederick C. Johlin, Jr., Iowa City, Iowa; P. Bruce McBrien, Winston-Salem, N.C.

[73] Assignee: Wilson-Cook Medical, Inc., Winston-Salem, N.C.

[21] Appl. No.: 702,062

[22] Filed: May 17, 1991

[51] Int. Cl.$^5$ ............................................... A61B 5/00
[52] U.S. Cl. ..................................... 128/772; 604/95
[58] Field of Search ................ 128/657, 772; 604/95, 604/281

[56] References Cited

U.S. PATENT DOCUMENTS

| | | | |
|---|---|---|---|
| 4,601,705 | 7/1986 | McCoy | 604/95 |
| 4,925,445 | 5/1990 | Sakamoto et al. | 604/95 |
| 4,951,686 | 8/1990 | Herlitze | 128/772 |
| 4,984,581 | 1/1991 | Stice | 128/772 |
| 5,066,285 | 11/1991 | Hillstead | 128/772 |

FOREIGN PATENT DOCUMENTS

| | | |
|---|---|---|
| 1435797 | 5/1976 | United Kingdom . |
| 9100051 | 1/1991 | World Int. Prop. O. ........ 128/772 |

OTHER PUBLICATIONS

Wilson-Cook Catalog, 1986-87, p. 20 "Wire Guided Papillotomes/Sphincterotomes".

*Primary Examiner*—Max Hindenburg
*Attorney, Agent, or Firm*—Woodard, Emhardt, Naughton, Moriarty & McNett

[57] ABSTRACT

Disclosed herein is an improved papillotome/sphincterotome procedure and a wire guide which is specially suited therefor. The disclosed wire guide includes an outer insulative tube of extruded teflon material, an inner shaft of nitinol, and a platinum coil at its distal end. The outer teflon tube has been extruded to have an internal dimension which is sized to loosely accommodate the inner shaft of nitinol with a cushion of air therebetween for additional insulative effect, and the platinum alloy coil is also loosely positioned within the teflon tubing. The nitinol material in the inner shaft has a high electrical resistivity which inhibits the flow of current, and also has superelastic characteristics which enhance the maneuverability of the guide. The nitinol shaft is tapered at its distal end where it is attached to the platinum alloy coil, which is radiopaque, allowing the tip to be readily viewed under radioscopic observation. The wire guide also has visual markings on its outer surface at 5 cm., 10 cm., 15 cm, whereby positioning can be verified endoscopically, and a marking 200 cm. from its distal end, whereby the general position of the guide relative to the endoscope can be determined by external visual observation.

20 Claims, 2 Drawing Sheets

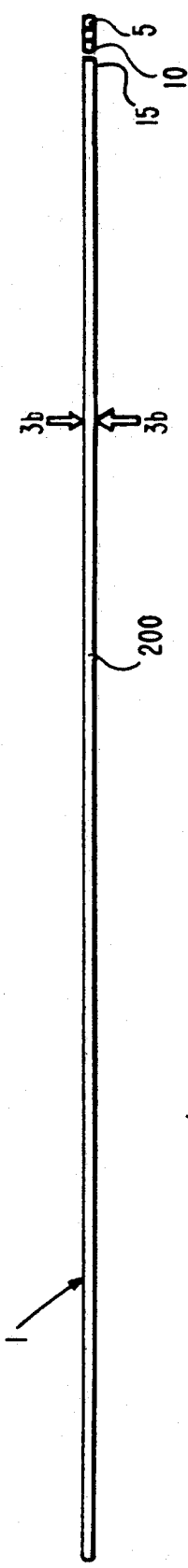
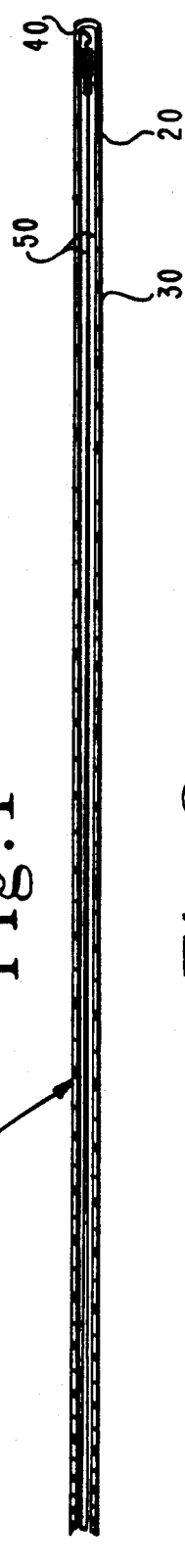
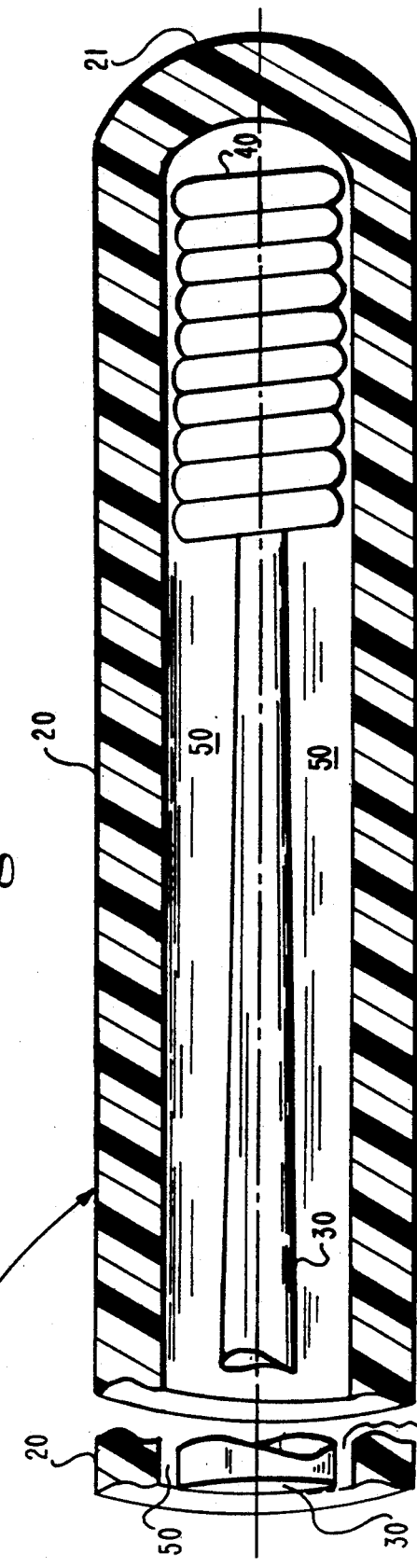
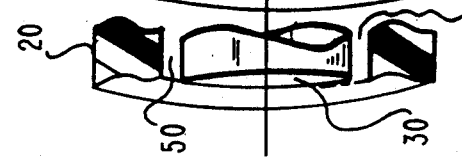

PAPILLOTOME/SPHINCTEROTOME PROCEDURES AND A WIRE GUIDE SPECIALLY SUITED THEREFOR

BACKGROUND OF THE INVENTION

1. Field of the Invention

The field of this invention is papillotome/sphincterotome procedures and medical wire guides used therewith.

2. Description of the Prior Art

Medical wire guides are used in a wide range of medical procedures. Such wire guides are generally used to gain and to maintain access into certain regions of the body where a medical procedure is to be performed. For instance, a wire guide would typically be used to gain access into a vein. A catheter can then be passed over the wire guide and into the vein where the catheter can be operated to perform its desired function within the vein.

One particular type of procedure in which wire guides are used is a papillotome/sphincterotome procedure, whereby surgical incisions may be remotely made through an endoscope. The surgical incision is usually assisted by means of an electrical current which is placed through a bowed wire at the distal end of the papillotome/sphincterotome instrument. With some papillotome/sphincterotome instruments, the incising device is guided into the desired position for making an incision with the aid of a wire guide. When a wire guide is used, it is commonly left in place while the papillotome/sphincterotome instrument is operated, since its positioning is useful for subsequently providing access for other devices.

Typically, standard wire guides have been used in conjunction with papillotome/sphincterotome procedures. The use of such wires guides, though, has had the effect of causing complications in the course of these procedures, and the use of standard wire guides as the source of these complications has generally gone unrecognized. What is needed is a wire guide that is specially suited for use in papillotome/sphincterotome procedures and which enhances the effectiveness and safety of such operations.

SUMMARY OF THE INVENTION

The present invention relates to improvements in papillotome/sphincterotome procedures and to a wire guide that is specially suited for such procedures. One aspect of the present invention relates to the fact that the electrical current applied to the incising wire of the papillotome/sphincterotome instrument can sometimes be shorted to, or induced into, a standard wire guide in place at the time of the incision. This shorted or induced current can cause the unintended burning of tissue by the wire guide itself. Prior to the present invention, this negative effect has generally gone unnoticed, or has failed to be traced to the use of the standard wire guide as the inadvertent cause of the injury. While the problem can be avoided by removing and repositioning the wire guide each time an incision is made, providing protection against injury with the wire guide remaining in place will bring beneficial results to the patient in the form of a safer and more effective operative procedure.

Wherefore, it is an object of the present invention to provide a papillotome/sphincterotome wire guide which reduces the risk of injury that might be caused by the shorting or inducing of current into the wire guide.

It is a further object of the present invention to provide such a wire guide that may be safely and reliably positioned within the body for accurate guidance of the papillotome/sphincterotome instrument.

It is a further object of the present invention to provide such a wire guide, the positioning of which can be readily ascertained by external visual observation.

It is yet a further object of the present invention to provide such a wire guide, the positioning of which can be readily ascertained under endoscopic and radioscopic observation.

These and other objects and advantages of the present invention will be apparent from a review of the following specification and claims.

BRIEF DESCRIPTION OF THE DRAWINGS

FIG. 1 is a side elevational view of one embodiment of the present invention.

FIG. 2 is a partially cross-sectioned and enlarged side elevational view of the distal end of the wire guide of FIG. 1.

FIG. 3a is a further enlarged side elevational view of the distal end of the wire guide of FIGS. 1 and 2. As in FIG. 2, the outer teflon tube 20 is cross-sectioned in FIG. 3a to expose the tapered nitinol inner core 30 and platinum alloy coil 40 and with air space 50 therebetween. FIG. 3b shows a portion of the body of wire guide 1, sectioned along lines 3b—3b in FIG. 1, with teflon tube 20 cross-sectioned to expose the untapered body portion of nitinol shaft 30 with air space 50 therebetween.

DESCRIPTION OF THE PREFERRED EMBODIMENT

Figure 4:
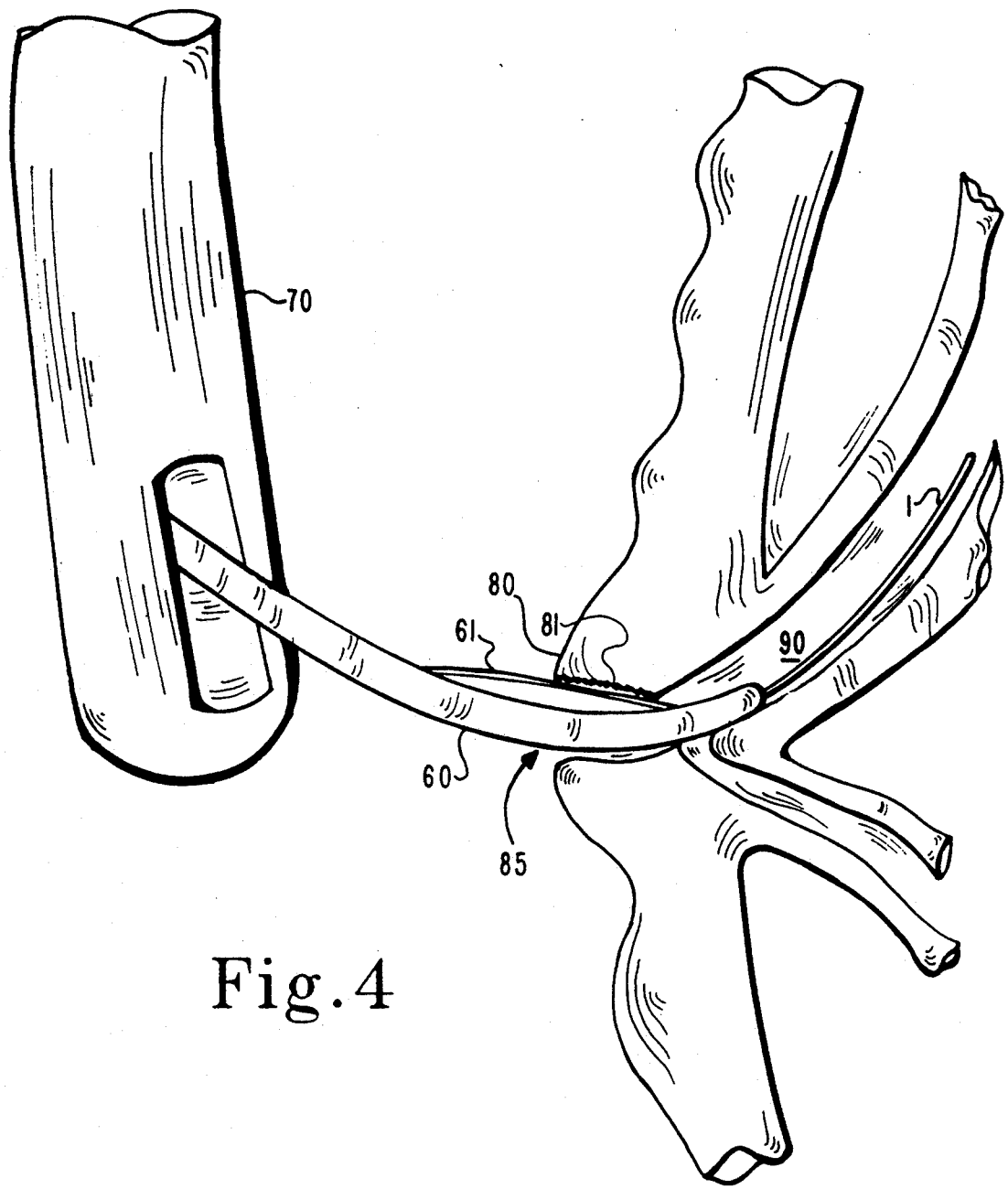
FIG. 4 is a view of a papillotome/sphincterotome instrument being operated to incise tissue at the papilla of Vater, with a wire guide according to the present invention being left in place during the incision procedure.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As illustrated in the drawings and described herein, wire guide 1 is specially suited to remain in place while a papillotome/sphincterotome incision is being made, thereby facilitating a safer and more efficient operative technique for such procedures. Wire guide 1 generally includes an outer tubular member 20 of extruded insulative material, an inner shaft 30 of material having high electrical resistivity, and a distal end coil 40 of material with high radiopacity. Outer tubular member 20 is made of extruded teflon material and has been extruded to have an internal dimension which is sized to loosely accommodate inner shaft 30 of material having high electrical resistivity with a space of air therebetween for additional insulative effect. Inner shaft 30 is tapered at its distal end and attached to coil 40, which is made of radiopaque material and which is also loosely positioned within the outer insulative tubular member 20. In one embodiment, wire guide 1 has an overall length of 480 cm. and has visual markings on its outer surface at 5 cm., 10 cm., 15 cm, and 200 cm. from its distal end.

There are a number of features in wire guide 1 which aid to reducing the risk that an electrical current will be shorted or induced into wire guide 1 that would cause a resulting shock to the patient. The outer tube 20 of extruded teflon serves as both an electrical and a thermal insulator, and air space 50 between teflon tube 20 and shaft 30 provides additional insulative effect. Using extruded teflon material is superior to the application of a coating of material in that imperfections in the coating process may provide a source for a short to occur, and that a coating process typically does not provide a uniformly thick layer of insulation. A uniform thickness of about 0.0065" in the wall of the extruded teflon has been found to provide sufficiently satisfactory results when used in combination with the other design aspects disclosed herein. The use of extruded tubular member 20 also allows for air space 50 which serves to further insulate inner shaft 30.

Inner shaft 30 is preferably made of material having high electrical resistivity. One particularly suitable material is nitinol, which has a high electrical resistivity to inhibit the flow of current that may be shorted or induced into shaft 30, and also has superelastic characteristics which enhance the maneuverability of wire guide 1. Nitinol shaft 30 is tapered at its distal end where it is attached to distal coil 40. The tapering at the distal end, in addition to enhancing the maneuverability of the tip of wire guide 1, also serves to reduce the chance of electrical shock to the patient in several further respects. The increased dimension of air space 50 increases the insulative effect in this area where harm to the patient is most likely to be caused by an electrical shock. Also, the decreased dimension of shaft 30 increases resistance to electrical flow, and reduces the potential for inductance into shaft 30, as well. In one example of the preferred embodiment, the tapering extends over the 12.7 cm distal end of shaft 30 from 0.021" to 0.006" in diameter in a wire guide having an overall outside diameter of 0.035". The nitinol material used is composed of about 55% Ni and 44% Ti, with trace elements of Cu (150 ppm), Fe (110 ppm), and Mn (21 ppm); and has an electrical resistivity in the range of 76-82 micro-ohm cm.

The use of a platinum alloy in distal coil 40, due to its high radiopacity, is particularly suited for this purpose in that it allows the tip to be readily viewed under radioscopic observation. It is to be further noted that the coiled configuration of distal coil 40 further serves to dissipate current, and provides a blunt tip which prevents the possible problem of where the distal tip of shaft 30 might accidentally be forced through the end portion 21 of tubular member 20. By maintaining distal coil 40 loosely within tubular member 20 with air space 50 therebetween, the risk that an electrical current will be shorted through the tip of wire guide 1 and into a patient is further reduced. In one example of the preferred embodiment, distal coil has an outer dimension of 0.018" within a tubular member 20 with a 0.022" inner diameter, and is composed of 92% Pt and 8% Ti.

Additionally, wire guide 1 has visual markings which aid in the positioning of wire guide 1 within the body. Markings 5, 10, and 15 are 5, 10, and 15 cm. respectively from the distal end of wire guide 1 and serve to facilitate the endoscopic observation of the relative positioning of wire guide within the body. Marking 200 is positioned 200 cm. from the distal end of wire guide 1, or roughly the length of the endoscopic channel of an endoscope, and allows for easy external visual determination of the relative location of wire guide 1 within the endoscope. By referencing marking 200, an operating physician can readily ascertain the relative general position of wire guide 1. This is particularly useful where wire guide 1 is left in place between successive papillotome/sphincterotome operative steps, and where different instrumentation is being removed and replaced over wire guide 1 through the endoscope.

By facilitating endoscopic and external visual determination of the relative positioning of wire guide 1, markings 5, 10, 15 and 200 serve to reduce the need for and duration of radioscopic or fluoroscopic observations, thereby reducing the attendant risks of radiation exposure.

FIG. 4 is a view of a papillotome/sphincterotome instrument 60 being operated to incise tissue at the papilla of Vater 80, where wire guide 1 has been left in place during the incision procedure. In FIG. 4, endoscope 70 has been positioned near the papilla of Vater 80 and wire guide 1 has been guided through endoscope 70, and has been positioned to gain access into the common bile duct 90 through the sphincter of Oddi 85. Papillotome/sphincterotome instrument 60 has been advanced over wire guide 1 through endoscope 70 and the sphincter of Oddi 85 into position for making an incision. In FIG. 4, electrical current is being placed through incising wire 61 to burn tissue 81 at the papilla of Vater 80, thereby opening access through this occluded passageway. While this procedure is occurring in FIG. 4, wire guide 1, which has the above described protective features, has been left in place within common bile duct 90, allowing for ease of access through the sphincter of Oddi 85 for subsequent operative steps.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. In a wire guided papillotome/sphincterotome procedure wherein a papillotome/sphincterotome instrument is introduced into position within the body through an endoscope with the aid of a wire guide and an incision is made by conducting an electrical current through an incising wire which is a part of the papillotome/sphincterotome instrument, the improvement comprising:

leaving said wire guide within the body while said incision is made, said wire guide being protective against inadvertent electrical shock that may be caused by the shorting or inducing of current from the incising wire into said wire guide, said wire guide including an outer tubular member of extruded insulative material, an inner shaft of material having high electrical resistivity, and a distal coil of radiopaque material; said outer insulative tube having an internal dimension which is sized to loosely accommodate said inner shaft with an insulative cushion of air therebetween; said inner shaft being tapered at its distal portion and attached to said distal coil at the distal end of said shaft; said distal coil being also loosely positioned within said tubular member of extruded insulative material and unattached to said tubular member with an insulative cushion of air therebetween.

2. The improvement in wire guided papillotome/sphincterotome procedures of claim 1 in which said extruded insulative material is made of teflon.

3. The improvement in wire guided papillotome/sphincterotome procedures of claim 1 in which said inner shaft of material is made from a superelastic metal.

4. The improvement in wire guided papillotome/sphincterotome procedures of claim 3 in which said inner shaft of material is made of nitinol.

5. The improvement in wire guided papillotome/sphincterotome procedures of claim 4 in which said extruded insulative material is made of teflon.

6. The improvement in wire guided papillotome/sphincterotome procedures of claim 5 in which said radiopaque material is a platinum alloy.

7. The improvement in wire guided papillotome/sphincterotome procedures of claim 1 in which said inner shaft of material is made of nitinol.

8. The improvement in wire guided papillotome/sphincterotome procedures of claim 1 in which said radiopaque material is a platinum alloy.

9. The improvement in wire guided papillotome/sphincterotome procedures of claim 1 in which said wire guide has a visual marking on its outer surface approximately 200 cm. from its distal end, whereby the general positioning of said wire guide relative to said endoscope can be determined by external visual observation.

10. The improvement in wire guided papillotome/sphincterotome procedures of claim 9 in which said wire guide additionally has visual markings on its outer surface approximately 5, 10, and 15 cm. from its distal end, whereby the positioning of said wire guide can be verified endoscopically.

11. A papillotome/sphincterotome wire guide protective against inadvertent electrical shock that may be caused by the shorting or inducing of electrical current from the incising wire of the papillotome/sphincterotome instrument into said wire guide, said wire guide including an outer tubular member of extruded insulative material, an inner shaft of material having high electrical resistivity, and a distal coil of radiopaque material; said outer insulative tube having an internal dimension which is sized to loosely accommodate said inner shaft with an insulative cushion of air therebetween; said inner shaft being tapered at its distal portion and attached to said distal coil at the distal end of said shaft; said distal coil being also loosely positioned within said tubular member of extruded insulative material and unattached to said tubular member with an insulative cushion of air therebetween.

12. The papillotome/sphincterotome wire guide of claim 11 in which said extruded insulative material is made of teflon.

13. The papillotome/sphincterotome wire guide of claim 11 in which said inner shaft of material is made from a superelastic metal.

14. The papillotome/sphincterotome wire guide of claim 13 in which said inner shaft of material is made of nitinol.

15. The papillotome/sphincterotome wire guide of claim 11 in which said inner shaft of material is made of nitinol.

16. The papillotome/sphincterotome wire guide of claim 11 in which said radiopaque material is a platinum alloy.

17. The papillotome/sphincterotome wire guide of claim 16 in which said extruded insulative material is made of teflon.

18. The papillotome/sphincterotome wire guide of claim 17 in which said inner shaft of material is made of nitinol.

19. The papillotome/sphincterotome wire guide of claim 18 in which said wire guide has a visual marking on its outer surface approximately 200 cm. from its distal end, whereby the general positioning of said wire guide relative to said endoscope can be determined by external visual observation.

20. The papillotome/sphincterotome wire guide of claim 19 in which said wire guide additionally has visual markings on its outer surface approximately 5, 10, and 15 cm. from its distal end, whereby the positioning of said wire guide can be verified endoscopically.

* * * * *